(12) United States Patent
Scarabaggio et al.

(10) Patent No.: US 8,426,352 B2
(45) Date of Patent: Apr. 23, 2013

(54) SCENTING COMPOSITION

(75) Inventors: Giovanni Scarabaggio, Pescara (IT); Italo Corzani, Chieti (IT); Yessica De Nardin, Pescara (IT); Juana Rios, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/088,443

(22) Filed: Apr. 18, 2011

(65) Prior Publication Data

US 2011/0263477 A1 Oct. 27, 2011

(30) Foreign Application Priority Data

Apr. 23, 2010 (EP) .................................... 10160962

(51) Int. Cl.
*A61Q 13/00* (2006.01)
(52) U.S. Cl.
USPC ............................................................ 512/1
(58) Field of Classification Search .................. 422/125, 422/14; 512/1
See application file for complete search history.

(56) References Cited

U.S. PATENT DOCUMENTS

| | | | | | |
|---|---|---|---|---|---|
| 5,574,821 | A | * | 11/1996 | Babasade | 392/392 |
| 6,143,707 | A | * | 11/2000 | Trinh et al. | 510/220 |
| 2008/0132625 | A1 | * | 6/2008 | Niehaus et al. | 524/285 |
| 2009/0041820 | A1 | * | 2/2009 | Wu et al. | 424/409 |
| 2010/0087357 | A1 | * | 4/2010 | Morgan et al. | 512/4 |
| 2011/0262317 | A1 | * | 10/2011 | Hofte et al. | 422/261 |

OTHER PUBLICATIONS

"The heat of fusion of polybutene-1" table 3, Howard W. Starkweather Jr., Glover A. Jones E. I. du Pont de Nemours and Company, Central Research and Development Department, Experimental Station, Wilmington, Delaware 19898. 6 Pages.

* cited by examiner

*Primary Examiner* — Ling Choi
*Assistant Examiner* — Lanee Reuther
(74) *Attorney, Agent, or Firm* — Tiffany M. Zerby; Steven W. Miller

(57) ABSTRACT

A scenting composition comprising a perfume and a polyolefin, the polyolefin having a crystallinity of from about 5% to about 60% and wherein the composition has a crystallinity of from about 0.5% to about 60%.

11 Claims, No Drawings

SCENTING COMPOSITION

RELATED APPLICATION

The present application claims priority under 35 U.S.C. §119 to EP 10160962.6 filed Apr. 23, 2010.

TECHNICAL FIELD

The present invention is in the field of scenting, especially it relates to a scenting composition, a product comprising the composition a method for scenting an appliance and the use of the composition to scent an appliance. The composition is especially suitable for use in appliances which involve high temperature and humidity conditions such as an automatic dishwashing machine.

BACKGROUND OF THE INVENTION

Items to be cleaned in an automatic dishwashing machine are soiled with food residues. The nature of the residues is quite diverse depending on the food that has been deposited on or cooked in the dishware/tableware. Usually the food residues have a plurality of malodours associated to them. Malodours can also come from food residues accumulated in dishwasher's parts such as the filter. The filter is usually a wet environment with food residues prone to bacteria degradation that usually have malodours associated to it.

The malodours can become evident during the automatic dishwashing operation either because there is superposition or combination of malodours that in terms give rise to other malodours and/or because the high temperature and humidity conditions found during an automatic dishwashing operation contribute to an easier perception of the malodours. Malodours can also be evident upon loading the dishwasher, especially if food residues degrade or rot.

Automatic dishwashing machines are usually placed in kitchens where users cook and frequently eat and they do not like to have unpleasant odours coming from the automatic dishwashing machine.

There is a need to reduce or eliminate the malodours that are generated during an automatic dishwashing operation and substitute the malodours by pleasant fragrance in the area surrounding the dishwasher during use.

Machine fresheners are known in the art. They are devices that hang in the dishwasher and release a perfume over time. The perfume release profile tend to be non-homogeneous over time, usually a high level of perfume is delivered at the beginning of the life of the freshener—that sometime can be overpowering—and the release profile can drop dramatically with time. In addition, the fluctuating temperature and humidity conditions found in an automatic dishwashing environment lead to some difficulties with some of the known machine fresheners.

The aim of the present invention is to overcome the above mentioned drawbacks.

SUMMARY OF THE INVENTION

According to a first aspect of the invention there is provided a scenting composition, by "scenting composition" is herein meant a product capable of delivering a pleasant smell such as a fragrance or perfume. The scenting product of the invention comprises a perfume and a polyolefin. The polyolefin preferably has a crystallinity of from about 5% to about 60%, more preferably from about 6% to about 50%, even more preferably from about 10% to about 40% and especially from about 10% to about 30%.

The scenting composition preferably has a crystallinity of from about 0.5% to about 60%, more preferably from about 1% to about 50%, even more preferably from about 5% to about 40% and especially from about 10% to about 30%.

The scenting composition provides a very uniform perfume delivery profile even under stressed conditions such as the high temperature and humidity condition found in an automatic dishwashing machine in operation. The composition would deliver perfume in a nearly constant manner during dishwashing operations and in between them. The composition also presents very good physical properties, it is quite malleable and pleasant to touch.

Preferably the composition has a melting point above about 70° C., more preferably above about 75° C. and especially above about 80° C. (measured as described herein below). This implies that the composition is solid and allows the formation of shaped solid bodies that provide sustained release of perfume.

The preferred polyolefin for use herein is polybutene-1. The term "polybutene-1" includes a homopolymer of butene-1 or a copolymer of butene-1 with another $\alpha$-olefin having 2 to 20 carbon atoms. In case of the copolymer, the ratio of another a-olefin to be copolymerized is 20 mole % or less, preferably 10 mole % or less and particularly preferably 5 mole % or less. Examples of another $\alpha$-olefin to be copolymerized include ethylene, propylene, hexene, 4-methylpentene-1, octene-1, decene-1, octadecene-1, etc. Especially preferred for use herein are copolymers of butane-1 and ethylene.

In preferred embodiments the composition comprises a wax, preferably a microcrystalline wax. Without being bound by theory, it is believed that wax, in particular microcrystalline wax, contribute to improve the physical properties of the composition, in particular the wax can contribute to reduce brittleness.

The composition of the invention can optionally comprise a nucleating agent. A nucleating agent is a processing aid that accelerates crystal formation reducing the processing times.

In preferred embodiments, the perfume comprises at least about 10%, more preferably at least about 20% and especially at least 30% by weight of the perfume of blooming perfume ingredients having a boiling point of less than 260° C. and a C log P of at least 3. The perfume would also typically comprise non-blooming perfume ingredients having a boiling point of more than 260° C. and a C log P of at least 3, preferably less than about 30%, more preferably less than about 25% and preferably between 5 and 20% by weight of the perfume of non-blooming perfume ingredients.

The perfume of the composition of the present invention are typically very effusive and consumer noticeable, leaving minimal residual perfume on the washed items, including dishes, glasses and cutlery, especially those made of plastic, rubber and silicone. The compositions can leave a residual perfume in the automatic dishwashing machine that can be enjoyed by the user in between dishwashing operations.

A blooming perfume ingredient is characterized by its boiling point (B.P.) and its octanol/water partition coefficient (P). The octanol/water partition coefficient of a perfume ingredient is the ratio between its equilibrium concentrations in octanol and in water. Since the partition coefficients of the preferred perfume ingredients herein have high values, they are more conveniently given in the form of their logarithm to the base 10, log P. The B.P. herein is determined at the normal, standard pressure of 760 mm Hg.

In preferred embodiments the composition comprises from about 20% to about 90%, more preferably from about 30% to about 70% and especially from about 35% to about 65% by weight thereof of polyolefin, preferably the polyolefin is polybutene-1. The composition preferably comprises from about 10% to about 60%, more preferably from about 20% to about 55% and especially from about 30% to about 50% by weight thereof of perfume. The composition preferably comprises from about 20% to about 60%, more preferably from about 25% to about 55% and especially from about 30% to about 50% by weight thereof of wax, preferably a microcrystalline wax.

According to a second aspect of the invention, there is provided an automatic machine freshener, preferably an automatic dishwashing machine freshener. The freshener has a very consistent perfume delivery profile over time. The perfume delivery during a dishwashing operation is very similar to that in between operations. The consumer gets a very pleasant scent when interacting with the automatic dishwasher, i.e. during loading and unloading.

According to a third aspect of the invention, there is provided an automatic machine freshener, preferably an automatic dishwashing machine freshener comprising a perfume and a polyolefin, preferably the polyolefin is polybutene-1.

According to a method aspect of the invention, the composition of the invention is used to fragrance and automatic appliance, the method is suitable for scenting environments in which the temperature rises significantly above room temperature. The method is especially suitable for scenting an automatic dishwashing machine, during a dishwashing operation and in between dishwashing operations.

According to the last aspect of the invention, the product of the invention is used for scenting an automatic dishwashing machine, during and in between operations.

The features of the scenting composition of the invention apply mutatis mutandis to the method and use aspects of the invention.

DETAILED DESCRIPTION OF THE INVENTION

The present invention envisages a scenting composition, a product comprising the composition, a method for scenting an appliance and the use of the composition to scent an appliance. The composition is especially suitable for use in appliances which involve high temperature and humidity conditions such as an automatic dishwashing machine. The composition of the invention provides a multitude of benefits. The scenting occurs during the operation of the appliance and in between operations. The composition is solid and it can be self-supported, i.e. it does not need a frame to support it, it can be used directed into an appliance, it can be placed in any part of the appliance, for example the cutlery basket of a dishwasher machine or it can have a holding means that allows the product to be hanged anywhere in an automatic dishwashing machine. As indicated herein before, the product provides a uniform perfume delivery profile over time, even under the high temperature and humidity conditions found in an automatic dishwashing machine.

An automatic dishwashing operation typically comprises three or more cycles: a pre-wash cycle, a main-wash cycle and one or more rinse cycles. The pre-wash is usually a cold water cycle, the main-wash is usually a hot water cycle, the water comes in cold and is heated up to about 55 or 65° C. Rinsing usually comprises two or more separate cycles following the main wash, the first being cold and, the final one starting cold with heat-up to about 65° C. or 70° C.

Polyolefin

Any semi-crystalline polyolefin having a crystallinity of from about 5% to about 60% is suitable for use herein. Preferred polyolefin for use herein is polybutene-1. The term "polybutene-1" includes any semi-crystalline homopolymers obtained by the polymerization of high-purity butene-1, preferably in the presence of a Ziegler-type catalyst. The term "polybutene-1" also includes copolymers of butene-1 with other polyolefin like ethylene, propylene, hexene, 4-methylpentene-1, octene-1, decene-1, octadecene-1, etc. Especially preferred polybutene-1 is a copolymer of polybutene-1 and ethylene.

The polybutene-1 for use herein is semi crystalline, and typically has high-molecular-weight, with a high degree of isotacticity that offers useful combinations of high heat resistance and freeze tolerance as well as flexibility, toughness, stress crack resistance and creep resistance. Polybutene-1 present slower setup times than those of other polyolefins, this seems to be because of its unique delayed crystallization, and by its polymorphism. High crystalinity olefins usually are not highly mixable with perfumes. Because of its unique crystallinity behavior polybutene-1 is mixable with perfumes at higher concentration than other polyolefins. When mixing the polybutene-1 with perfume in the certain amount as here disclosed the crystals formation is further delayed as well as the rate of formation is decreased but not totally. The final mixture can retain some of the mechanical properties of the polybutene-1.

Preferred polybutene-1 for use herein includes DP8510M and DP8911 supplied by Basell-Lyondel. Especially preferred for use herein is DP8911.

Crystallinity

The degree of crystallinity has a great influence on hardness, density, transparency, softening point and diffusion of solid materials. Many polymers have both a crystalline and amorphous regions. In these cases, crystallinity is specified as a percentage of the mass of the material that is crystalline with respect to the total mass.

Crystallinity can be measured using x-ray diffraction techniques and differential scanning calorimetry (DSC).

For example, methods ASTM E 793-06 (Enthalpies of Fusion and Crystallization by Differential Scanning Calorimetry) or ASTM F 2625-07 (Measurement of Enthalpy of Fusion, Percent Crystallinity, and Melting Point of Ultra-High-Molecular Weight Polyethylene by Means of Differential Scanning Calorimetry) can be used to determine the Enthalpy of Fusion and then the crystallinity of the polyolefin and the composition of the invention. For the purpose of this invention, crystallinity is measured following ASTM E 793-06. The crystallinity of a polyolefin is calculated against published values of the 100% crystalline corresponding material. For example, in the case of polybutene-1 the enthalpy of fusion of 100% crystalline material (stable form I) is 135 J/g (ref. "The heat of fusion of polybutene-1" table 3, Howard W. Starkweather Jr., Glover A. Jones E. I. du Pont de Nemours and Company, Central Research and Development Department, Experimental Station, Wilmington, Del. 19898).

To measure the crystallinity of the composition, a sample of it must be first conditioned for 15 days at 23° C. in a sealed aluminum bag to avoid perfumes loosing over time. Then a DSC analysis is run according the method ASTM E 793-06 (temperature rate 10° C./min) to measure the enthalpy of fusion of the composition. In order to have an indication of where the reference peak of the DSC of the composition should be found a DSC of the current polyolefin of the mixture is run to determine the melting point of the polyolefin.

The enthalpy of fusion of the composition sample is then normalized by dividing the obtained value by the weight of the sample to get the specific enthalpy of fusion by gram of sample (i.e. J/g) and then by dividing again this latter value by the standard 100% polybutene-1 crystalline material enthalpy of fusion value (i.e. 135 J/g) to finally get the crystallinity of the composition.

It has to be noted that many DSC instruments are able to calculate directly both the normalized enthalpy of fusion of the sample and the crystallinity.

The crystallinity of the polybutene-1 is measured in an analogous manner.

Melting Point

The melting point of the composition of the invention is determined using the standard method ASTM D-4440 (Dynamic Mechanical Properties Melt Rheology). The method consists in measuring the rheological properties of a composition disc specimen in a temperature range (from 25° C. to 100° C.). The disc specimen has the same diameter of the parallel plate geometry used in the measurement. A 25 mm disc is used. The discs are prepared previously using plastic frames with 25 mm discs hole and 2 mm thickness. The composition is melt and poured in the disc frames. Exceeding material is removed with a spatula. The sample is then cooled down and stored for 24 hr at 23° C. in a climatic room and in sealed aluminum bags. The rheometer used is a SR5 Stress controlled (Rheometrics®). The "melting point" (also referred as melting at crossover point) of a viscous-elastic material like the composition of the invention is defined as the temperature value at which the "liquid/viscous characteristic part" (known as loss modulus G") and the "rigid/solid characteristic part" (known as elastic modulus G') are equal.

Perfume

Any perfume is suitable for use in the product of the invention, any of the current compositions used in perfumery. These can be discreet chemicals; more often, however, they are more or less complex mixtures of volatile liquid ingredients of natural or synthetic origin. The nature of these ingredients can be found in specialised books of perfumery, e.g. in S. Arctander (Perfume and Flavor Chemicals, Montclair N.J., USA 1969).

The perfumes herein can be relatively simple in their composition or can comprise highly sophisticated, complex mixtures or natural and synthetic chemical components.

Wax

Suitable wax for use herein includes paraffin wax, long-chain alkanes, esters, polyesters and hydroxy esters of long-chain primary alcohols and fatty acids, naphthenic and iso-paraffinic long chain hydrocarbons, petrolatum. They can be natural or synthetic. The waxes are excellent oil binding allowing perfume incorporation in the composition at high levels.

Commercial waxes include beeswax, carnauba wax, petroleum waxes, microcrystalline wax, petroleum jelly and polyethylene waxes. Especially preferred for use herein is a microcrystalline wax. Preferred commercial material includes Permulgin 4201 supplied by Koster Keunen (Holland)

Nucleating Agent

Nucleating agents accelerate the formation of crystals in polymers containing polybutene and copolymers thereof. Nucleating agents promote the growth of the crystal by lowering the activation energy required for crystal organization. By using nucleating agents, the nucleation starts occurring at a higher temperature than in the polyolefin containing composition without nucleating agents. Further during the cooling phase, the number of polymer crystals increases as well as the final distribution result more uniform than in the case in which no nucleating agent is used. Suitable nucleating agents include talc, benzoates, phosphate ester salts, sorbitol derivatives, or commercial products like Hyperform® HPN-20E, Hyperform® HPN-68L by Milliken Co.

Optional components to be added to the product of the invention include tackifying resins, as those described in US 2008/0132625 A1, paragraph [0020], plasticizers, as those described in US 2008/0132625 A1, paragraph [0023]. If present the tackifying resin would be in a level of from about 1% to about 50% wt. If present the plasticizer would be in a level of from about 1% to about 50% wt. Further additives can be incorporated into the product of the invention in quantities of up to 15 wt % in order to vary certain properties. These can be, for example, dyes, pigments, or fillers such as titanium dioxide, talcum, clay, chalk, and the like. They can also, for example, be stabilizers or adhesion promoters.

EXAMPLES

The following compositions in accordance with the invention are prepared:

Example 1

50 grams of Polybutene-1 grade DP8911M, supplied by LyondellBasell Industries are added to 50 grams of perfume, the resulting product is mixed at 85° C. for 4 h and then cooled down.

Example 2

60 grams of Polybutene-1 grade DP8911M, supplied by LyondellBasell Industries are added to 40 grams of perfume, the resulting product is mixed at 85° C. for 4 h and then cooled down.

Example 3

2000 ppm nucleating agent (Hyperform® HPN-68L supplied by Milliken Co) is added to a composition similar to that of Example 2, the mixture is processed in a similar manner.

Example 4

40 grams of Polybutene-1 grade DP8911M, supplied by LyondellBasell Industries are added to 30 grams of perfume and 30 grams of wax Permulgin 4201 supplied by Koster Keunen, the resulting product is mixed at 85° C. for 2 h and then cooled down.

Example 5

Wax Low Level 40 grams of Polybutene-1 grade DP8911M, supplied by LyondellBasell Industries are added to 50 grams of perfume and 10 grams of wax Permulgin 4201 supplied by Koster Keunen, the resulting product is mixed at 85° C. for 2 h and then cooled down.

All the compositions provide a uniform perfume delivered profile and present good mechanical properties.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A product for scenting an automatic dishwashing machine comprising:
   a.) a scenting composition comprising from about 10% to about 60% by weight of the composition of a perfume and a polyolefin, the polyolefin having a crystallinity of from about 5% to about 50% and wherein the composition has a crystallinity of from about 0.5% to about 60%; and
   b.) a holder that allows the scenting composition to be hung in the automatic dishwashing machine.

2. The product according to claim 1 wherein the composition has a melting point of above about 70° C.

3. The product according to claim 1 wherein the polyolefin is polybutene-1.

4. The product according to claim 3 comprising from about 0.5% to about 60% by weight thereof of the wax.

5. The product according to claim 1 further comprising a wax.

6. The product according to claim 5 comprising from about 0.001% to about 10% by weight thereof of a nucleating agent.

7. The product according to claim 1 further comprising a nucleating agent.

8. The product according to claim 1 wherein the perfume comprises at least about 20% by weight thereof of blooming perfume ingredients having a boiling point of less than 260° C. and a C log P of at least 3.

9. The product according to claim 1 wherein the perfume comprises less than about 30% by weight thereof of non-blooming perfume ingredients having a boiling point of more than 260° C. and a C log P of at least 3.

10. The product according to claim 1 comprising from about 20% to about 90% by weight thereof of the polyolefin.

11. The product according to claim 1 comprising from about 10% to about 60% by weight thereof of the perfume.

* * * * *